United States Patent [19]

Ueda et al.

[11] Patent Number: 4,889,721

[45] Date of Patent: Dec. 26, 1989

[54] SUSTAINED-RELEASE PERCUTANEOUS PREPARATIONS

[75] Inventors: Yoshio Ueda, Kobe; Sotoo Asakura, Kyoto; Yoshio Murakami, Takatsuki; Toshiomi Nakate, Minoo, all of Japan

[73] Assignee: Fujisawa Pharmaceutical Co., Ltd., Osaka, Japan

[21] Appl. No.: 219,365

[22] Filed: Jul. 15, 1988

[30] Foreign Application Priority Data

Jul. 24, 1987 [JP] Japan .................. 62-185790

[51] Int. Cl.⁴ .............................. A61F 13/02
[52] U.S. Cl. .................... 424/448; 424/447; 424/449
[58] Field of Search ............. 424/448, 449, 447

[56] References Cited

U.S. PATENT DOCUMENTS

| | | | |
|---|---|---|---|
| 3,742,951 | 7/1973 | Zaffaroni | 424/434 |
| 3,982,946 | 9/1976 | Maekawa | 430/225 |
| 4,432,802 | 2/1984 | Harata et al. | 424/461 |
| 4,443,497 | 4/1984 | Samejima et al. | 427/213.36 |
| 4,540,701 | 8/1985 | Ueda et al. | 514/357 |
| 4,575,548 | 3/1986 | Ueda | 536/46 |
| 4,749,574 | 6/1988 | Ueda et al. | 424/448 |

FOREIGN PATENT DOCUMENTS

| | | |
|---|---|---|
| 193164 | 9/1986 | European Pat. Off. . |
| 241806 | 10/1987 | European Pat. Off. . |
| 59-20374 | 7/1982 | Japan . |
| 60-156607 | 1/1984 | Japan . |
| 61-30517 | 7/1984 | Japan . |

OTHER PUBLICATIONS

*Chemical Abstracts,* vol. 100, #161803n (1986).
Search Report for European Patent Application 88 11 1816.
Dictionaire 'Vidal', 60th Ed., 1984, p. 1439, Paris, FR Column 2: "Trintrine 10 mg–6.5 mg–2.5 mg Laleuf".

*Primary Examiner*—Jose G. Dees
*Assistant Examiner*—Leon R. Horne
*Attorney, Agent, or Firm*—Oblon, Spivak, McClelland, Maier & Neustadt

[57] ABSTRACT

Sustained-release percutaneous preparations which have at least two adhesive layers and in which a drug is contained in the layer farthest from the skin and a solid powder is dispersed in an adhesive layer other than the layer farthest from the skin provide slow release of the drug. By varying the kind and concentration of the solid powder, the rate of release of the drug from the preparations can be controlled.

10 Claims, No Drawings

SUSTAINED-RELEASE PERCUTANEOUS PREPARATIONS

This invention relates to a sustained-release percutaneous preparations and more particularly to a sustained-release percutaneous preparation which has at least two adhesive layers wherein a solid powder is contained as dispersed in one of said adhesive layers other than the layer farthest from the skin on application and a drug is contained at least in said layer farthest from the skin on application. The preparations find application in the field of health care.

Percutaneous drug delivery systems adapted to release a drug gradually to achieve a sustained therapeutic effect and reduce the risk of side effect have recently been a favorite subject of research, and there are known a preparation such that the release of a drug is controlled by a polymeric film (Japanese Examined Patent Application No. 9003/1976) and a preparation such that the release of a drug is controlled by more than one superimposed layers of dissimilar adhesive polymers (Japanese Unexamined Patent Application KOKAI Nos. 7413/1982, 206516/1983 and 20374/1984.

Regarding the above preparation where the release of a drug is controlled by a polymeric film, the presence of pinholes in the polymeric film would result in a massive release of the drug at a time so that there are risks of side effects developing depending on kinds of drugs.

As to the preparation such that the release of a drug is controlled by a superimposion of adhesive layers of dissimilar types, there may be incompatibility according to combinations of the drug and adhesive polymers, thus imposing limitations on adhesive polymers that can be used.

Futhermore, since the release of a drug is dependent on the selected combination of a drug with a polymeric base in both of the above types of preparations, it is difficult to assure a controlled rate of drug release.

The intensive research by the present inventors for overcoming the above disadvantages revealed that when the preparation is such that it contains at least two adhesive layers, one of the layers other than the farthest from the skin on application containing a solid powder as dispersed therein and a drug being contained in the layer farthest from the skin on application, the drug can be released at a controlled rate and even according to zero-order kinetics and that by varying the quantity and type of solid powder to be dispersed, the rate of release of the drug can be varied as desired. This invention has been accomplished on virtue of the above findings.

The drug to be contained in an adhesive layer of the sustained-release percutaneous preparations according to this invention is preferably soluble in the adhesive agent used. Thus, for example, corticosteroids, anesthetics, antihistaminics, antibacterial agents, antifungal agents, analgesic-antiinflammatory agents, keratolytics, vitamins, antispasmodics, etc., as well as systemic drugs such as anticonvulsants, sedatives, sex hormones, antidiabetics, antihypertensives, antibiotics, central nervous system acting drugs, vasodilators, etc. may be mentioned. According to their types, these drugs are used in appropriate amounts for achieving the desired therapeutic effect.

Among said corticosteroids are prednisolone acetate, prednisolone, hydrocortisone acetate, hydrocortisone, dexamethasone, fluocinolone acetonide, betamethasone, beclometasone dipropionate, fludroxycortide, fluocinonide and so on. The anesthetics include benzocaine, lidocaine, ethyl aminobenzoate and so on. Among said antihistaminics are diphenhydramine hydrochloride, isothipendyl hydrochloride, diphenylimidazole and so on. On the other hand, benzalkonium chloride, nitrofurazone, etc. may be mentioned as said antibacterial agents. The antifungal agents include nystatin, undecylenic acid and so on. Among said analgesic-antiinflammatory agents are indomethacin, methyl salicylate, glycol salicylate, salicylamide, sodium salicylate and so on.

Regarding said keratolytic agents, vitamin A and antispasmodics, there may be mentioned salicylic acid, vitamin A, atropine, methscopolamine bromide and so on. As to said systemic drugs, hypertensives such as reserpine, clonidine, propranolol, metoprolol tartarate, etc.; antibiotics such as erythromycin, chloramphenicol, cefalexin, cefazolin, ceftizoxime, tetracycline, neomycin sulfate, oxytetracycline, penicillin,etc.; central nervous system acting drug such as barbiturate, diazepam, nitrazepam, chlorpromazine, etc., and vasodilators such as nitroglycerin, nifedipine, 2-nitroxymethyl-6-chloropyridine and its $\beta$-cyclodextrin inclusion compound, isosorbide dinitrate, diltiazem hydrochloride, dipyridamole, isosorbide dinitrate, etc. may be mentioned.

The solid powder may be any particles which does not cause the incompatibility with the drug used and do not cause adverse effects on the skin, but are preferably not soluble in the adhesive used. Thus, for example, talc, kaolin, silica, sericite, metal oxides (for example, titanium oxide, zinc oxide, magnesium oxide, etc.), inorganic salts (for example, calcium carbonate, magnesium carbonate, sodium carbonate, calcium sulfate, magnesium sulfate, calcium phosphate, etc.) and synthetic polymers (for example, methacrylic resin, nylon, polyethylene, etc.), and natural or semisynthetic polymers (for example, chitin, chitosan, $\beta$-cyclodextrin, etc.) may be mentioned.

There is no particular limitation on the particle size of such solid powder but the range of about 0.5 to 30 $\mu$m is preferred. The adhesive may be any of those that can be used for the usual medical tapes. Thus, for example, silicone adhesives (such as Silicone 355 ®, Dow Corning Corp.), rubber adhesives (such as JSR0585 ®, Japan Synthetic Rubber Co., Ltd. ), acrylic ester adhesives (Carbond ®, Dainippon Ink and Chemicals, Inc.; Primal ® N580S, Japan Acrylic Chemical Co.,Ltd., etc.) and so on can be selectively employed.

The content of the drug or of the solid powder in the sustained-release percutaneous preparations of the invention is practically optional and can be selected in accordance with the properties of the drug, the desired duration of action and other factors. Generally speaking, however, their content may range from 0.1 to 50 weight percent and 5 to 80 weight percent, respectively, and preferably from 1 to 30 weight percent and 10 to 60 weight percent, respectively.

For the purpose of improving the solubility and diffusibility of the drug in the adhesive layer, the sustained-release percutaneous preparations according to the invention may contain glycols (principally for increasing the solubility of the drug), such as diethylene glycol, propylene glycol, glycerol, polyethylene glycol, etc., oils and fats (primally for promoting the diffusion of the drug), such as olive oil, squalene, lanolin, etc., alcohols such as ethyl alcohol, isopropyl alcohol, etc., esters such as isopropyl myristate etc., and unsturated fatty acids such as oleic acid, linolic acid and so on.

Aside from these, various additives which are generally incorporated in percutaneous preparations of this type can also be added.

The sustained-release percutaneous preparations according to this invention can be manufactured by the established procedures for the manufacture of medical tapes in general.

For example, a mixture of the drug and an adhesive is applied on an appropriate drug-impermeable support such as a synthetic resin film, a composite synthetic resin-metal film or a metal (such as aluminum foil) to give a first layer.

After drying of the layer, a mixture of a solid powder and an adhesive is applied on top of the first layer to provide a second layer, which is then dried. If necessary, for the purpose of improving the bond strength with respect to the skin, an adhesive containing neither the drug nor the solid powder is further coated to provide a third layer, which is then dried.

In this arrangement, the drug is generally incorporated in a layer other than the layer in which said solid powder is dispersed, that is to say in the layer to be disposed farthest from the skin on application, but where a certain degree of early onset of action is desired according to the type of drug, the drug may be advantageously incorporated in the layer in which the solid powder is incorporated. The adhesive may be the same or different for the respective layers.

It should be understood that by using different adhesives for the respective layers, a percutaneous preparation further differing in the rate of drug release can be manufactured.

Below set forth are results of a test carried out with representative preparations, which illustrate the effects of the invention.

Release Test

Test Preparations

A: The preparation according to Example 1
B: The preparation according to Example 2
C: The preparation according to Example 3
D: The preparation according to Example 4
E: The preparation according to Example 5
F: The preparation according to Reference 1
G: The preparation according to Reference 2

Method

An in vitro ointment release test apparatus designed to allow a release solvent maintained at a predetermined temperature to flow in contact with the test preparation (3.6 cm$^2$) in a constant direction was used as the test setup. As the release solvent, distilled water at 35° C. was passed at a flow rate of 0.6 ml/min. The determination was made by the ultraviolet method (268 nm).

Test Results

| Test prepa-ration | Release rate (%) | | | | | | | | |
|---|---|---|---|---|---|---|---|---|---|
| | 0.5 H | 1 H | 2 H | 3 H | 4 H | 6 H | 8 H | 22 H | 24 H |
| A | 2.6 | 3.9 | 6.3 | 8.3 | 10.2 | 13.6 | 16.6 | 32.1 | 33.4 |
| B | 2.0 | 3.2 | 4.5 | 6.9 | 8.8 | 11.7 | 14.4 | 26.7 | 28.6 |
| C | 0.4 | 0.6 | 1.0 | 1.5 | 1.7 | 3.0 | 4.1 | 13.1 | 14.6 |
| D | 2.3 | 4.5 | 8.2 | 10.5 | 14.1 | 20.6 | 26.4 | 58.0 | 65.7 |
| E | 2.7 | 4.3 | 6.8 | 9.2 | 10.7 | 13.7 | 16.7 | 32.6 | 36.9 |
| F | 20.5 | 27.5 | 40.4 | 47.9 | 52.6 | 63.0 | 71.5 | 88.8 | 99.5 |
| G | 8.5 | 13.4 | 20.0 | 26.1 | 29.2 | 37.4 | 44.1 | 69.9 | 71.8 |

The above data indicate that the sustained-release percutaneous preparations according to the invention (test preparations A through E) release the drug more slowly than the preparations containing no solid powder (test preparations F and G) and approximately release the drug according to the zero-order kinetics.

It was also found that by varying the level of addition of solid powder (A vs. B), the rate of release of the drug from the preparations of this invention can be controlled as desired and that by varying the kind of solid powder (B vs. C and D vs. E) and the kind of adhesive (B vs. D and C vs. E), any desired rate of drug release can be obtained.

EXAMPLES

The following examples are further illustrative of the invention.

EXAMPLE 1

Using a knife coater, a mixture of 2-nitroxymethyl-6-chloropyridine (10 g) and acrylic ester adhesive (Carbond ®, Dainippon Ink and Chemicals Co., Ltd.) (40 g) is coated on an aluminum foil support in a thickness of 0.5 mm to provide a first layer.

Then, a mixture of talc (16.7 g) and the same acrylic ester adhesive as above ( 33.3 g) is coated on top of the first layer in a thickness of 0.5 mm to provide a second layer. The above procedure gives a sustained-release percutaneous preparation having the following formula per cm$^2$.

| [First layer] | |
|---|---|
| 2-Nitroxymethyl-6-chloropyridine | 10 mg |
| Acrylic ester adhesive | 40 mg |
| [Second layer] | |
| Talc | 16.7 mg |
| Acrylic ester adhesive | 33.3 mg |

EXAMPLE 2

The same procedure as Example 1 was followed to provide a sustained-release percutaneous preparation having the following formula per cm$^2$.

| [First layer] | |
|---|---|
| 2-Nitroxymethyl-6-chloropyridine | 10 mg |
| Acrylic ester adhesive | 40 mg |
| [Second layer] | |
| Talc | 25 mg |
| Acrylic ester adhesive | 25 mg |

EXAMPLE 3

The same procedure as Example 1 was followed to provide a sustained-release percutaneous preparation having the following formula per cm$^2$.

| [First layer] | |
|---|---|
| 2-Nitroxymethyl-6-chloropyridine | 10 mg |
| Acrylic ester adhesive | 40 mg |
| [Second layer] | |
| Methacrylic resin particles | 25 mg |
| Acrylic ester adhesive | 25 mg |

EXAMPLE 4

The same procedure as Example 1 was followed to provide a sustained-release percutaneous preparation having the following formula per cm².

| [First layer] | |
|---|---|
| 2-Nitroxymethyl-6-chloropyridine | 10 mg |
| Acrylic ester adhesive (Carbond ®) | 40 mg |
| [Second layer] | |
| Talc | 25 mg |
| Silicone adhesive (Silicone 355 ®) | 25 mg |

EXAMPLE 5

The same procedure as Example 1 was followed to provide a sustained-release percutaneous preparation having the following formula per cm².

| [First layer] | |
|---|---|
| 2-Nitroxymethyl-6-chloropyridine | 10 mg |
| Acrylic ester adhesive (Carbond ®) | 40 mg |
| [Second layer] | |
| Methacrylic resin particles | 25 mg |
| Silicone adhesive (Silicone 355 ®) | 25 mg |

EXAMPLE 6

The same procedure as Example 1 was followed to provide a sustained-release percutaneous preparation having the following formula per cm².

| [First layer] | |
|---|---|
| Inclusion compound of 2-nitroxymethyl-6-chloropyridine with β-cyclodextrin | 10 mg |
| Acrylic ester adhesive | 40 mg |
| [Second layer] | |
| Talc | 25 mg |
| Acrylic ester adhesive | 25 mg |

EXAMPLE 7

The same procedure as Example 1 was followed to provide a sustained-release percutaneous preparation having the following formula per cm².

| [First layer] | |
|---|---|
| Inclusion compound of 2-nitroxymethyl-6-chloropyridine with β-cyclodextrin | 10 mg |
| Acrylic ester adhesive | 40 mg |
| [Second layer] | |
| Methacrylic resin particles | 25 mg |
| Acrylic ester adhesive | 25 mg |

EXAMPLE 8

The same procedure as Example 1 was followed to provide a sustained-release percutaneous preparation having the following formula per cm².

| [First layer] | |
|---|---|
| Inclusion compound of 2-nitroxymethyl-6-chloropyridin with β-cyclodextrin | 10 mg |
| Acrylic ester adhesive (Carbond ®) | 40 mg |
| [Second layer] | |
| Talc | 25 mg |
| Silicone adhesive (Silicone 355 ®) | 25 mg |

EXAMPLE 9

The same procedure as Example 1 was followed to provide a sustained-release percutaneous preparation having the following formula per cm².

| [First layer] | |
|---|---|
| Inclusion compound of 2-nitroxymethyl-6-chloropyridine with β-cyclodextrin | 10 mg |
| Acrylic ester adhesive (Carbond ®) | 40 mg |
| [Second layer] | |
| Methacrylic resin particles | 25 mg |
| Silicone adhesive Silicone 355 ® | 25 mg |

Reference 1

Using a knife coater, a mixture of 2-nitroxymethyl-6-chloropyridine (10 g) and acrylic ester adhesive (Carbond ®, Dainippon Ink and Chemicals Co., Ltd.) (40 g) was coated on an aluminum foil support in a thickness of 0.5 mm to give a percutaneous preparation having the following formula per cm².

| 2-Nitroxymethyl-6-chloropyridine | 10 mg |
|---|---|
| Acrylic ester adhesive | 40 mg |

Reference 2

The procedure of Example 1 was followed to provide a first layer. Then, a silicone adhesive (Silicone 355 ®, Dow Corning Co.) was coated on top of the first layer in a thickness of 0.5 mm to give a percutaneous preparation having the following formula per cm².

| [First layer] | |
|---|---|
| 2-Nitroxymethyl-6-chloropyridine | 10 mg |
| Acrylic ester adhesive | 40 mg |
| [Second layer] | |
| Silicone adhesive | 50 mg |

What is claimed is:

1. A sustained-release percutaneous preparation which has at least two adhesive layers wherein a solid powder is dispersed in one of said adhesive layers other than the layer farthest from the skin on application and a drug is contained at least in said layer farthest from the skin on aplication, wherein said adhesive is an acrylic ester adhesive and/or a silicone adhesive.

2. A sustained-release percutaneous preparation according to claim 1 which has two adhesive layers wherein the solid powder is dispersed in the adhesive layer contiguous to the skin on application and the drug is contained in the other adhesive layer.

3. A sustained-release percutaneous preparation according to claim 1 or 2 wherein the solid powder is talc or methacrylic resin.

4. A sustained-release percutaneous preparation according to calim 1 or 2 wherein the drug is 2-nitroxymethyl-6-chloropyridine.

5. A sustained-release percutaneous preparation according to calim 1 or 2 wherein the drug is an inclusion compound of 2-nitroxymethyl-6-chloropyridine with β-cyclodextrin.

6. A sustained-release percutaneous preparation according to claim 3 wherein the adhesive is an acrylic ester adhesive and/or a silicone adhesive.

7. A sustained-release percutaneous preparation according to claim 3 wherein the drug is 2-nitroxymethyl-6-chloropyridine.

8. A sustained-release percutaneous preparation according to claim 4 wherein the drug is 2-nitroxymethyl-6-chloropyridine.

9. A sustained-release percutaneous preparation according to claim 3 wherein the drug is an inclusion compound of 2-nitroxymethyl-6-chloropyridine with β-cyclodextrin.

10. A sustained-release percutaneous preparation according to claim 4 wherein the drug is an inclusion compound of 2-nitroxymethyl-6-chloropyridine with β-cyclodextrin.

* * * * *